(12) United States Patent  (10) Patent No.: US 7,865,232 B1
Krishnaswamy et al.  (45) Date of Patent: Jan. 4, 2011

(54) METHOD AND SYSTEM FOR AUTOMATICALLY CALIBRATING ISCHEMIA DETECTION PARAMETERS

(75) Inventors: Harish Krishnaswamy, Mountain View, CA (US); Anil Keni, Bakersfield, CA (US)

(73) Assignee: Pacesetter, Inc., Sylmar, CA (US)

( * ) Notice: Subject to any disclaimer, the term of this patent is extended or adjusted under 35 U.S.C. 154(b) by 734 days.

(21) Appl. No.: 11/835,256

(22) Filed: Aug. 7, 2007

(51) Int. Cl.
*A61N 1/362* (2006.01)
(52) U.S. Cl. .................. 600/509; 600/508; 600/515; 600/516; 600/521
(58) Field of Classification Search ......... 600/508–509, 600/515–516, 521
See application file for complete search history.

(56) References Cited

U.S. PATENT DOCUMENTS

| | | | |
|---|---|---|---|
| 4,228,803 A | 10/1980 | Reckards | |
| 4,712,555 A | 12/1987 | Thornander et al. | |
| 4,759,367 A | 7/1988 | Callaghan | |
| 4,858,610 A | 8/1989 | Callaghan et al. | |
| 5,135,004 A | 8/1992 | Adams et al. | |
| 5,199,428 A | 4/1993 | Obel et al. | |
| 5,203,326 A | 4/1993 | Collins | |
| 5,243,981 A | 9/1993 | Hudrlik | |
| 5,251,621 A | 10/1993 | Collins | |
| 5,313,953 A | 5/1994 | Yomtov et al. | |
| 5,388,578 A | 2/1995 | Yomtov et al. | |
| 5,497,780 A | 3/1996 | Zehender | |
| 5,531,768 A | 7/1996 | Alferness | |
| 6,016,443 A | 1/2000 | Ekwall et al. | |
| 6,021,350 A | 2/2000 | Mathson | |
| 6,108,577 A | 8/2000 | Benser | |
| 6,112,116 A | 8/2000 | Fischell et al. | |
| 6,115,628 A | 9/2000 | Stadler et al. | |
| 6,128,526 A | 10/2000 | Stadler et al. | |
| 6,233,486 B1 | 5/2001 | Ekwall et al. | |
| 6,256,538 B1 | 7/2001 | Ekwall | |
| 6,264,606 B1 | 7/2001 | Ekwall et al. | |
| 6,272,379 B1 | 8/2001 | Fischell et al. | |
| 6,301,496 B1 | 10/2001 | Reisfeld | |
| 6,324,421 B1 | 11/2001 | Stadler et al. | |
| 6,368,284 B1 | 4/2002 | Bardy | |
| 6,381,493 B1 | 4/2002 | Stadler et al. | |
| 6,468,263 B1 | 10/2002 | Fischell et al. | |
| 6,473,647 B1 | 10/2002 | Bradley | |
| 6,501,983 B1 | 12/2002 | Natarajan et al. | |
| 6,931,281 B2 | 8/2005 | Bradley et al. | |
| 6,937,899 B2 | 8/2005 | Sheldon et al. | |
| 2002/0143262 A1 | 10/2002 | Bardy | |
| 2005/0059897 A1 | 3/2005 | Snell et al. | |
| 2006/0009811 A1 | 1/2006 | Sheldon et al. | |

(Continued)

FOREIGN PATENT DOCUMENTS

EP 0839544 B1 7/2003

(Continued)

*Primary Examiner*—Carl H Layno
*Assistant Examiner*—Deborah Malamud

(57) ABSTRACT

A method and system for automatically determining ischemia detection parameters are provided. The method includes obtaining a baseline trace indicative of a cardiac behavior, determining an ischemia detection window based on at least one physiologic state indicator within the baseline trace, and automatically identifying a fiducial point based on the baseline segment trace. The baseline trace includes a baseline segment within the ischemia detection window; where the ischemia detection window and the fiducial point may constitute ischemia detection parameters.

16 Claims, 15 Drawing Sheets

U.S. PATENT DOCUMENTS

2006/0116593 A1  6/2006  Zhang et al.

FOREIGN PATENT DOCUMENTS

| | | |
|---|---|---|
| EP | 1164933 B1 | 5/2006 |
| WO | WO 00/57781 | 10/2000 |
| WO | WO 03/020366 A1 | 3/2003 |
| WO | WO 03/020367 A1 | 3/2003 |
| WO | WO 2004/047917 A1 | 6/2004 |

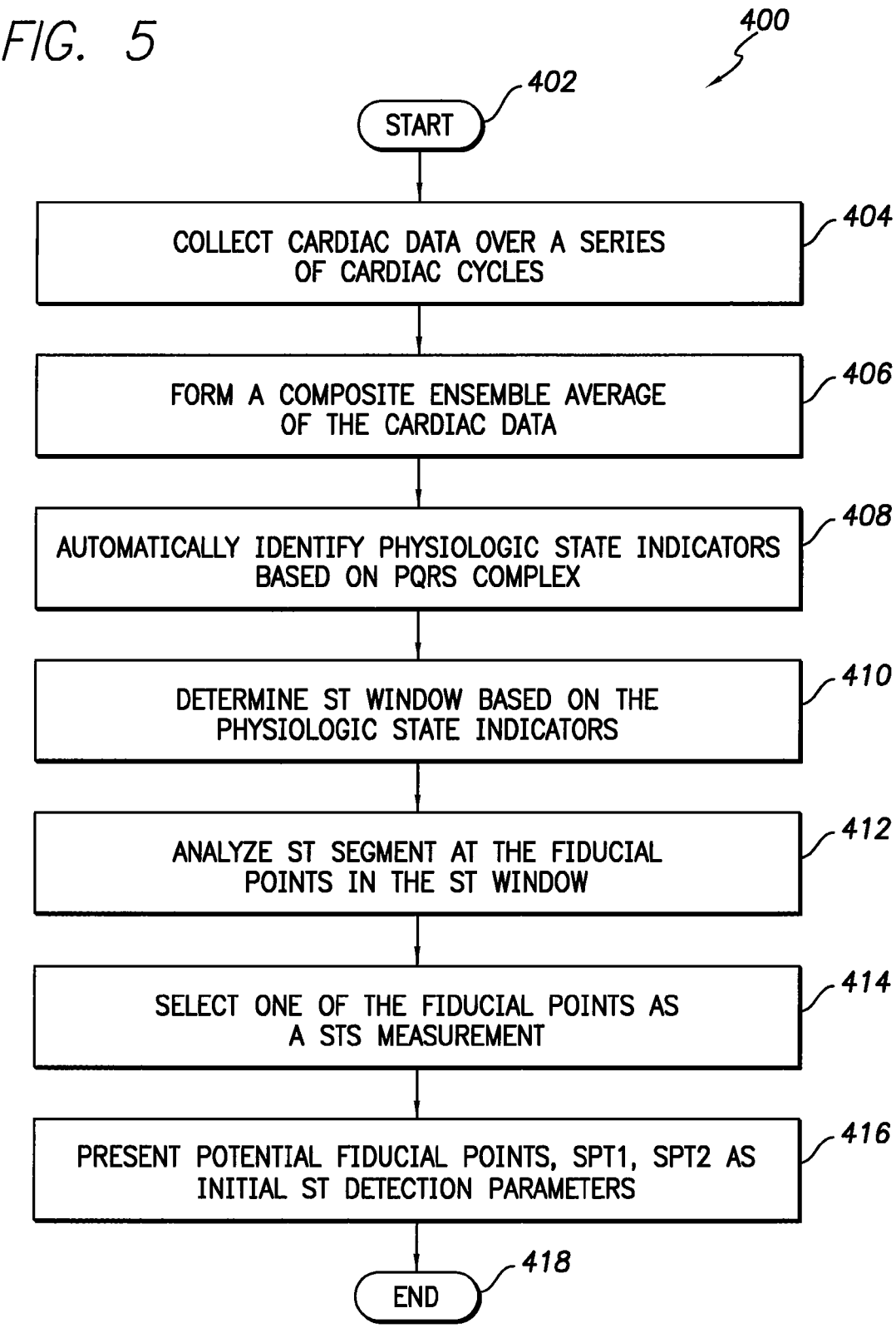

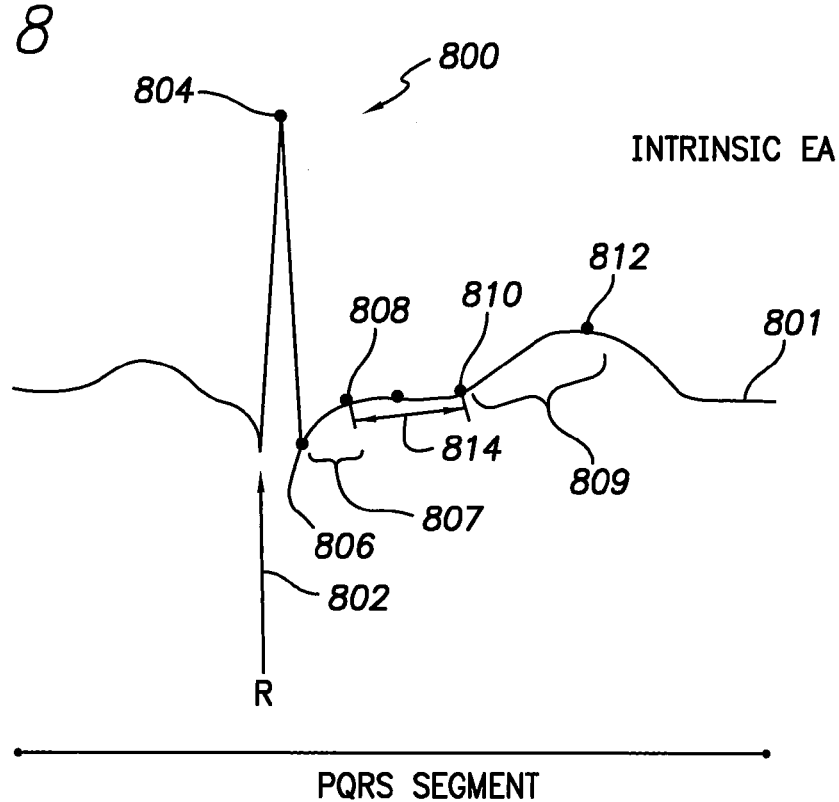
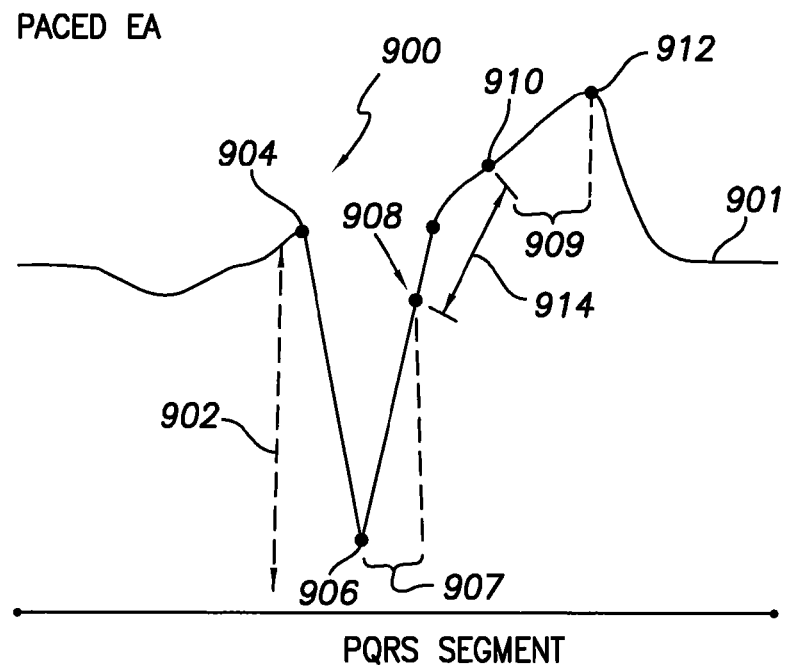

METHOD AND SYSTEM FOR AUTOMATICALLY CALIBRATING ISCHEMIA DETECTION PARAMETERS

BACKGROUND OF THE INVENTION

Embodiments of the present invention pertain generally to implantable medical devices, and more particularly pertain to implantable medical devices that automatically calibrate ischemia detection parameters.

Many patients at risk of cardiac ischemia have pacemakers, ICDs or other medical devices implanted therein. Electrocardiograms (ECG) are useful for diagnosing ischemia and locating damaged areas within the heart. Cardiac ischemia is a condition whereby heart tissue does not receive adequate amounts of oxygen and is usually caused by a blockage of an artery leading to heart tissue. ECGs are composed of various waves and segments that represent the heart depolarizing and repolarizing. ST segment represents the portion of the cardiac signal between ventricular depolarization and ventricular repolarization. While P-waves, R-waves and T-waves may be generally considered features of a surface electrocardiogram (ECG), for convenience and generality, herein the terms R-wave, T-wave and P-wave are also used to refer to the corresponding internal cardiac signal, such as an intra-cardiac electrogram (IEGM).

Techniques have been developed for detecting cardiac ischemia using implanted medical devices. Some conventional IEGM-based ischemia detection techniques seek to detect ischemia by identifying changes in the elevation or depression of the ST segment from the baseline of the IEGM that occur during cardiac ischemia. Elevation or depression of the ST segment in an IEGM may result when there are abnormalities in the polarizations of cardiac tissue during an acute myocardial infraction (MI). An ST segment shift arises because of differences in the electric potential between cells that have become ischemic and those cells that are still receiving normal blood flow. Deviation of the ST segment from a baseline is a result of injury to cardiac muscle, changes in the synchronization of ventricular muscle depolarization, drug or electrolyte influences, or the like.

However, not all ST segment shifts are indicative of MI or other injury to the cardiac muscle. Instead, a ST segment shift above or below the baseline may result because of "axis shifts", electrical noise, cardiac pacing, high sinus or tachycardia cardiac rates that distort the IEGM waveform. Techniques have been developed for detecting cardiac ischemia using implanted medical devices. However, conventional pacemakers or defibrillators do not monitor disease progression by using a running average of cardiac cycles to determine shifts in the ST segment. Furthermore, typical pacemakers require a user to manually set an isoelectric point, which drifts from patient to patient; thereby preventing any automatic determination of ST shift.

However, conventional approaches to ischemic events have not satisfactorily determined ischemia using ST segment shifts. A need remains for improved methods and systems to detect an acute shift in the ST segment of an intracardiac electrogram, where an ST segment and a fiducial point may be automatically detected and used to determine an ST shift that can be used to assess the existence or exacerbation of a myocardial ischemia.

SUMMARY

In accordance with at least one embodiment, a method is provided for automatically determining ischemia detection parameters. The method includes obtaining a baseline trace indicative of a cardiac behavior, determining an ischemia detection window based on at least one physiologic state indicator within the baseline trace, and automatically identifying a fiducial point based on the baseline segment trace. The baseline trace includes a baseline segment within the ischemia detection window; and the ischemia detection window and fiducial point constitute ischemia detection parameters.

Optionally, the method may provide locating physiologic state indicators within the baseline trace that define boundaries for the ischemia detection window. The physiologic state indicator may be located by successively comparing adjacent points along the baseline composite trace with one another. Furthermore, the physiologic state indicators represent a second slope change following at least one of an R-wave marker and a V-wave marker. Alternatively, the physiologic state indicator may be located by identifying a derivative of the baseline composite trace. In addition, the method may include determining the fiducial point within the baseline segment by analyzing potential fiducial points and identifying the potential fiducial point that yields a desired relation between the baseline segment and new segment traces. A fiducial point may be located that gives a maximum difference between data values of the baseline segment and an actual segment traces during a ST window.

Additionally, the method may collect cardiac data over a series of cardiac cycles and form a baseline composite trace based on the cardiac data. The forming may include obtaining an ensemble average of the cardiac data over a series of cardiac cycles, and the baseline composite trace may represent a running average that is continuously updated.

In accordance with another embodiment, a system for automatically determining ischemia detection parameters is provided. The system includes memory for storing the cardiac signals that represent the cardiac activity of a patient over a period of time. The system also includes a processor that is configured to obtain a baseline composite trace indicative of cardiac behavior, determine an ischemia detection window based on at least one physiologic state indicator within the baseline composite trace, and to automatically identify a fiducial point based on the baseline segment trace and ischemia detection window. The trace includes a baseline segment within the ischemia detection window. The system further provides an output to present potential ischemia detection parameters.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 5 illustrates a flow diagram for a method for automatically determining ischemia detection in accordance with an embodiment of the present invention.

FIG. 8 illustrates a composite intrinsic baseline signal shown in FIG. 6B along with ischemia detection parameters and a ST window utilized in accordance with an embodiment of the present invention.

FIG. 9 illustrates a composite paced baseline signal shown in FIG. 7B along with ischemia detection parameters and a ST window utilized in accordance with an embodiment of the present invention.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
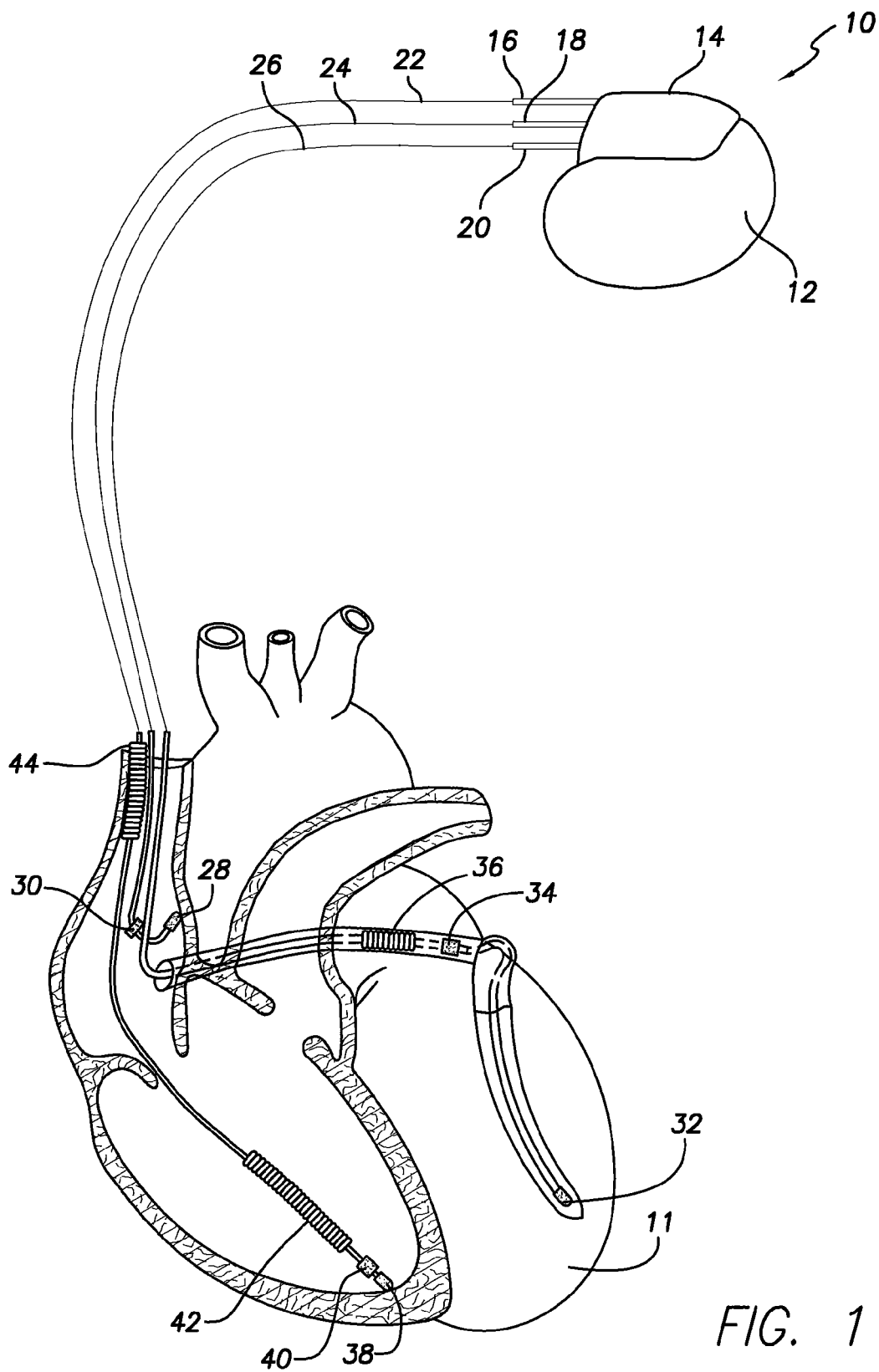
FIG. 1 illustrates an implantable medical device formed in accordance with an embodiment of the present invention.

FIG. 1 illustrates an implantable medical device 10 (IMD) that is coupled to a heart 11. The implantable medical device 10 may be a cardiac pacemaker, an implantable cardioverter defibrillator ("ICD"), a defibrillator, or an ICD coupled with a pacemaker implemented in accordance with an embodiment of the present invention. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and based thereof, to identify potentially abnormal physiology (e.g., ischemia). The detected cardiac signals may include intrinsic heart beats that have no assistance from any type of manmade electrical stimulation. Alternatively, the detected cardiac signals may include heart beats that have been stimulated by an electrical source to produce a paced heartbeat. The electrical source that provides the paced heartbeat may include an implantable device that provides low energy electrical signals, such as provided by a pacemaker, a demand pacemaker, a single-chamber pacemaker, a dual chamber pacemaker, a biventricular pacemaker, and the like. Optionally, the paced heartbeat may be generated by an implantable device that provides high energy electrical signals such as those provided by an implantable cardioverter defibrillator.

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or both to measure the physiological condition of the heart 11. One or more of the leads 22, 24 and 26 detect intra-cardiac electrogram (IEGM) signals that form an electrical activity indicator of myocardial function over multiple cardiac cycles. To sense atrial cardiac signals and to provide right atrial chamber stimulation therapy, the right atrial lead 24 having at least an atrial tip electrode 28, which is typically implanted in the right atrial appendage, and an atrial ring electrode 30. The IEGM signals represent analog signals that are subsequently digitized and analyzed to identify waveforms of interest. Examples of waveforms identified from the IEGM signals include the P-wave, T-wave, the R-wave, the QRS complex and the like. The waveforms of interest may be collected over a period of time, either continuously or at defined intervals.

The coronary sinus lead 26 receives atrial and ventricular cardiac signals and delivers left ventricular pacing therapy using at least a left ventricular tip electrode 32, left atrial pacing therapy using at least a left atrial ring electrode 34, and shocking therapy using at least a left atrial coil electrode 36. The right ventricular lead 22 has a right ventricular tip electrode 38, a right ventricular ring electrode 40, a right ventricular (RV) coil electrode 42, and a SVC coil electrode 44. Therefore, the right ventricular lead 22 is capable of receiving cardiac signals, and delivering stimulation in the form of pacing and shock therapy to the right ventricle.

IMD 10 may be used to collect cardiac signals (e.g., both intrinsic and paced heart beats). Initially, the IMD 10 may collect baseline cardiac signals and processor 60 (shown in FIG. 2) may determine ST segment variations for the baseline signals. The baseline cardiac signals and ST segment variations may be stored in memory 94 (shown in FIG. 2). The IMD 10 may have to be reprogrammed by a programmer (shown in FIG. 3 in order for the IMD 10 to properly monitor the cardiac signals and provide the correct paced heartbeat. The IMD 10 may obtain cardiac signals (e.g., IEGM) on a beat-by-beat basis and store each heart beat in memory 94

Figure 2:
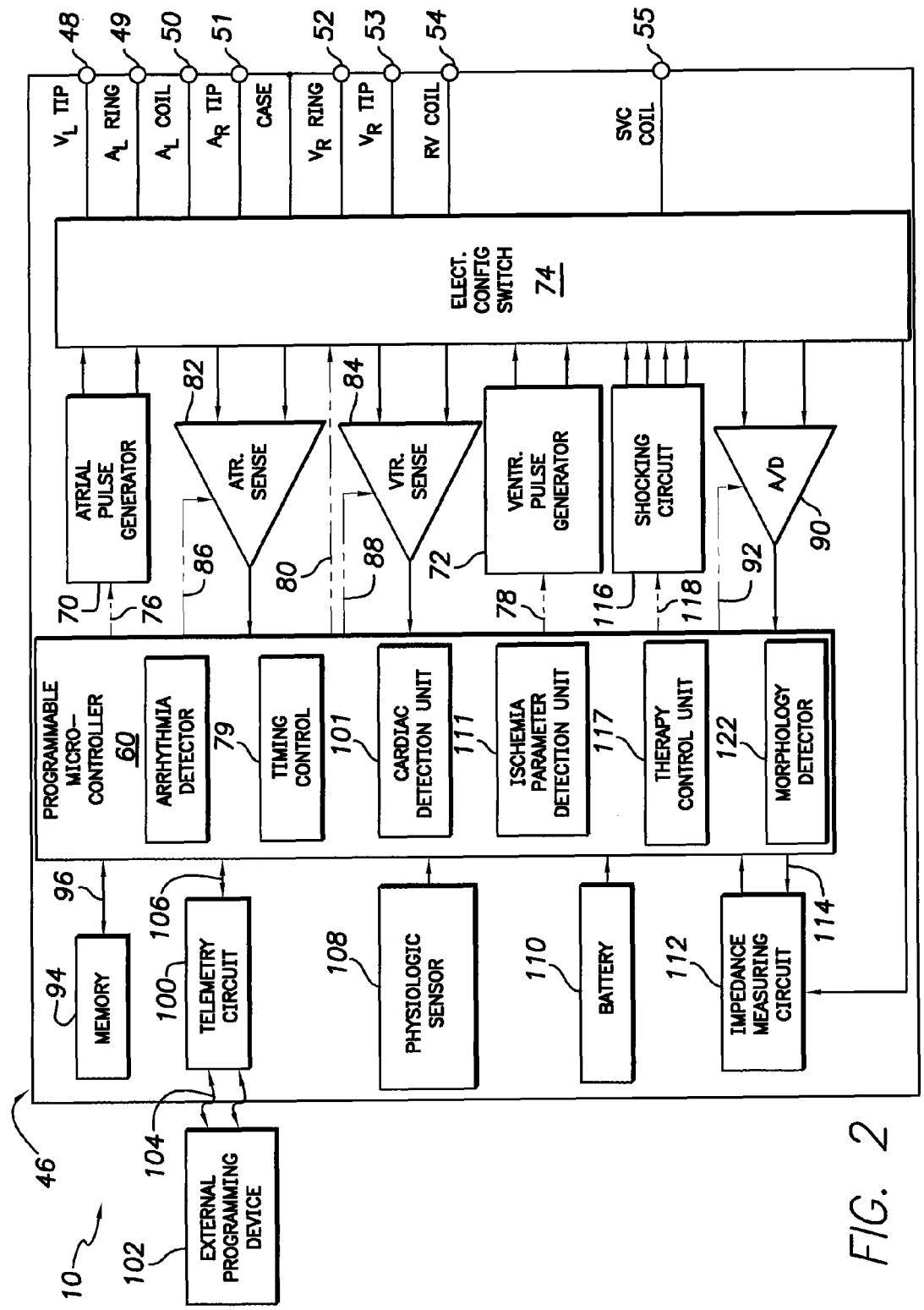
FIG. 2 illustrates a functional block diagram of exemplary internal components of an implantable medical device formed in accordance with an embodiment of the present invention.

(shown in FIG. 2). In addition, associated with each heart beat, IMD 10 may store the time the heart beat occurred and the heart rate of the heart beat. Processor 60 (shown in FIG. 2) may determine the ST segment variation associated with the heart beat and store the ST segment value in memory 94.

FIG. 2 illustrates a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation and/or pacing stimulation.

The housing 46 for IMD 10 (shown schematically in FIG. 2), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial shocking terminal ($A_L$ COIL) 50, a right ventricular tip terminal ($V_R$ TIP) 53, a right ventricular ring terminal ($V_R$ RING) 52, a right ventricular shocking terminal ($R_V$ COIL) 54, and an SVC shocking terminal (SVC COIL) 55.

The IMD 10 includes a programmable microcontroller 60, which controls the operation of the IMD 10 based on acquired cardiac signals. For example, the microcontroller 60 includes a cardiac detection unit 101 to monitor the cardiac signals and to identify therein ST segment shifts and determine potential ischemic and AMI conditions. The microcontroller 60 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (e.g., data) as controlled by a program code stored in memory. Among other things, the microcontroller 60 receives, processes, and manages storage of digitized data from the various electrodes. The microcontroller 60 may also analyze the data, for example, in connection with collecting, over a period of time, reference ST segment shifts in a cardiac signal (e.g., sense signals received from leads 22, 24 and 26).

As explained below in connection with FIGS. 5-10, the microcontroller 60 obtains a baseline composite trace indicative of cardiac behavior. The baseline composite trace saved in memory 94 may be based on an ensemble average (e.g., a running average). The microcontroller 60 obtains an ensemble average of the cardiac data over a series of cardiac cycles, and may continuously update the ensemble average, which is saved in memory 94. The micro controller 60 includes an ischemia parameter detection unit 111 that determines physiologic state indicators, determines a start and an end for an ischemic detection window based on the physiological state indicators, and automatically identifies a fiducial point for a baseline segment trace within the ischemia detection window. The start and end for the ischemia detection window and the fiducial point represent ischemia detection parameters. As explained below in connection with FIGS. 5-10, the ischemia parameter detection unit 111 may determine the start and end of an ST window as the ischemia detection window. The start and end of the ST window maybe identified based on a shape of the baseline composite trace, such as by identifying certain local minimum and maximum in the baseline composite trace.

The microcontroller 60 uses the ischemia detection parameters to measure ST segment shifts and compares them to an ST threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like).

The IMD 10 includes an atrial pulse generator 70 and a ventricular/impedance pulse generator 72 to generate pacing stimulation pulses. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

Switch 74 includes a plurality of switches for connecting the desired electrodes to the appropriate I/O circuits, thereby providing complete electrode programmability. Atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits, 82 and 84, that are connected to the microcontroller 60. In this manner, the atrial and ventricular sensing circuits, 82 and 84 are able to trigger or inhibit the atrial and ventricular pulse generators, 70 and 72.

The cardiac signals are applied to the inputs of an analog-to-digital (A/D) data acquisition system 90. The cardiac signals maybe IEGM signals or ECG signals. The data acquisition system 90 is configured to acquire IEGM signals, convert the raw analog data into a digital IEGM signals, and store the digital IEGM signals in memory 94 for later processing and/or telemetric transmission to an external device 102. Memory 94 may also store a variable threshold value 120 and a ST threshold 122. Control signal 92 from processor 60 determines when the A/D 90 acquires signals, stores them in memory 94 or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The cardiac detection unit 101 receives the cardiac signals from A/D 90 and determines the onset and determination of an ischemic or AMI condition based on a ST segment deviation. The cardiac cycle is composed of a P-wave, a Q-wave, an R-wave, an S-wave, and a T-wave. The portion of the signal between the S-wave and T-wave constitutes a ST segment. The ST segment may have a voltage level that aligns with the voltage level of a baseline heart rhythm. Alternatively, the ST segment may have a voltage level that is shifted above or shifted below the baseline. ST segment variations indicate a potential coronary episode. ST segment variations may include ST deviations or ST shifts. A ST deviation is determined by subtracting an average PQ segment (e.g., the isoelectric segment) voltage from the ST segment voltage for a heartbeat. The ST deviation provides a measure of the change in variability over a period of time. An ST shift is determined by changes in the ST deviation over a period of time. For example, a current ST shift may be calculated by subtracting a stored baseline ST deviation from a newly acquired ST deviation. ST deviations and ST shifts may be calculated as averages over multiple cardiac cycles as well.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may also store data indicative of myocardial function, such as the IEGM data, ST segment shifts, reference ST segment shifts, and the like for a desired period of time (e.g., one hour, 24 hours, one month, and the like).

Memory 94 may also store large amounts of data in order to determine an ischemic detection parameters. For instance, memory 94 may store raw cardiac data, from both intrinsic heart beats and paced heart beats, that is used to generate baseline cardiac signals. Memory 94 may store the baseline cardiac signals and may also updates to each baseline cardiac signal. In addition, the following may be stored in memory 94: a R-wave marker, a V-wave marker, a fiducial point, a ST window start point, a ST window end point, a ST window, a ST segment trace, baseline segments, a predefined offset, physiologic state indicators, ischemia detection parameters, and the like. The memory 94 may also store instructions that direct the microcontroller 60 to analyze the cardiac data to detect ischemia and/or to identify events of interest.

The operating parameters of the IMD 10 may be non-invasively programmed into the memory 94 through a telemetry circuit 100 in communication with the external device 102, such as a programmer (shown in FIG. 3), trans-telephonic transceiver or a diagnostic system analyzer. The telemetry circuit 100 is activated by the microcontroller 60 by a control signal 106. The telemetry circuit 100 allows intracardiac electrograms, and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 which is enabled by the microcontroller 60 via a control signal 114. The impedance measuring circuit 112 is advantageously coupled to the switch 74 so that impedance at any desired electrode may be obtained.

In the case where IMD 10 is intended to operate as an implantable cardioverter/defibrillator (ICD) device, the IMD 10 detects the occurrence of an ST segment shift that indicates an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (e.g., up to 0.5 joules), moderate (e.g., 0.5-10 joules) or high energy (e.g., 11 to 40 joules), as controlled by the microcontroller 60. Such shocking pulses are applied to the heart 11 of the patient through at least two shocking electrodes, and as shown in this embodiment, selected from the left atrial coil electrode 36, the RV coil electrode 42, and/or the SVC coil electrode 44.

Figure 3:
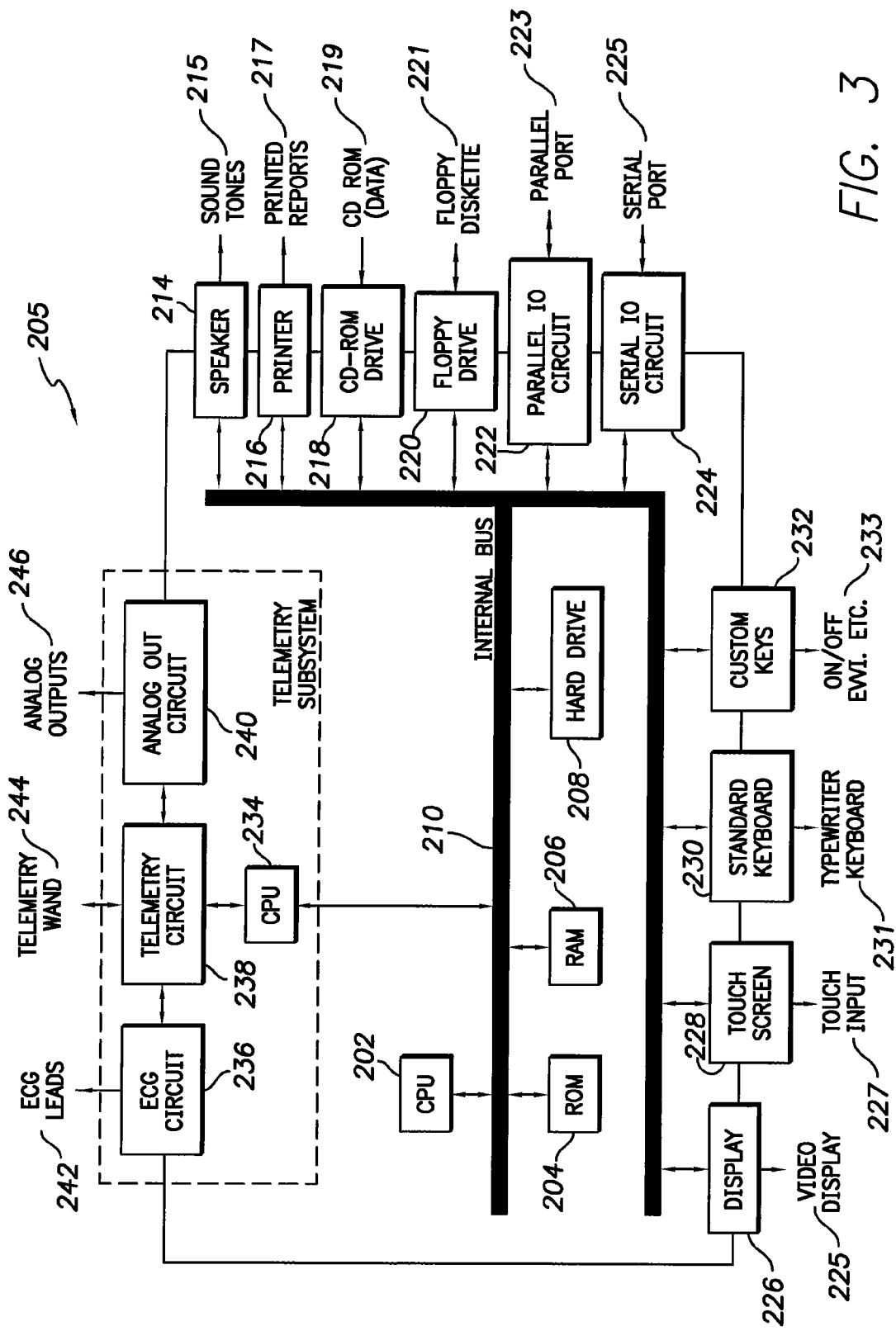
FIG. 3 illustrates a functional block diagram of certain components of an external programmer used to communicate with the implantable medical device shown in FIG. 1 utilized in accordance with an embodiment of the present invention.

FIG. 3 illustrates a functional block diagram of an external device 200, such as a programmer, that is operated by a physician, a health care worker, or a patient to interface with IMD 10. The external device 200 may be utilized in a hospital setting, a physician's office, or even the patient's home to communicate with the IMD 10 to change a variety of operational parameters regarding the therapy provided by the IMD 10 as well as to select among physiological parameters to be monitored and recorded by the IMD 10. Further, the external device 200 may be utilized to interrogate the IMD 10 to determine the condition of a patient, to adjust the physiological parameters monitored, or to adapt the therapy to a more efficacious one in a non-invasive manner. For example, the external device 200 may change the operating mode of the IMD 10, such that the IMD 10 collects and stores data, for example, on a beat-by-beat basis instead of capturing a cardiac sample every hour. Alternatively, the external device 200 may obtain pre-recorded cardiac signals from the memory 94 of IMD 10 (shown in FIG. 2) that were recorded at an earlier time. Furthermore, the external device 200 may be used to monitor in real-time the heart beat (e.g., intrinsic as well as paced) as collected by the surface ECG unit 342.

The external device 200 maybe used to program, into the IMD 10, information used by the IMD 10 to calculate ischemia detection parameters. For example, the external device 200 maybe used to program the offsets, from the slope changes in the baseline trace, to the start and end points for the ST segment window. The external device 200 may also be used to program information associated with calculation of the fiducial point.

The external device 200 may store the raw cardiac information (e.g., cardiac signals, associated heart rate, time the heart beats occurred, and the like) received from IMD 10 or ECG unit 342 in RAM 206 or hard drive 208. Alternatively, the external device 200 may transfer the raw cardiac information as well as composite baseline traces, physiologic state indicators, an R-wave marker, a V-wave marker, a fiducial point, a ST start point, a ST end point, ST segment trace, predefined offsets, ischemia detection parameters, and the like, via the telemetry subsystem 212 to IMD 10 or via the Internet 336 (shown in FIG. 4) to a database 324 for storage.

The external device 200 may process the raw cardiac information) and store the processed information (e.g., ST segment variations associated with heart rate on a beat-by-beat basis) on hard drive 208, as well as display the processed information as described below. For example, the external device 200 may process stored cardiac data and implement the process discussed below in connection with FIGS. 5-10 to calculate the ischemia detection parameters. Optionally, the external device 200 may transfer the raw cardiac information (e.g., cardiac signals, associated heart rate, time the heart beats occurred, and the like) via the internet 336 (shown in FIG. 4) for a user workstation 346 or server 332 for processing to determine ST segment variation associated with heart rate on a beat-by-beat basis.

External device 200 includes an internal bus 210 that connects/interfaces with a Central Processing Unit (CPU) 202, ROM 204, RAM 206, a hard drive 208, a speaker 214, a printer 216, a CD-ROM drive 218, a floppy drive 220, a parallel I/O circuit 222, a serial I/O circuit 224, a display 226, a touch screen 228, a standard keyboard connection 230, custom keys 232, and a telemetry subsystem 212. The internal bus 210 is an address/data bus that transfers information (e.g., either memory data or a memory address from which data will be either stored or retrieved) between the various components described. The hard drive 208 may store operational programs as well as data, such as reference ST segments, ST thresholds, timing information and the like.

The CPU 202 typically includes a microprocessor, a microcontroller, or equivalent control circuitry, designed specifically for controlling interfacing the external device 200 with the IMD 10. The CPU 202 may further include RAM or ROM memory, logic and timing circuitry, state machine circuitry, and I/O circuitry to interface with the IMD 10. Typically, the microcontroller 60 includes the ability to process or monitor input signals (data) as controlled by program code stored in memory (e.g., ROM 206).

In order for a physician or health care worker to communicate with the external device 200, a display 226, a touch screen 228, a standard keyboard 230, and custom keys 232 are provided. The display 226 (e.g., may be connected to a video display 225) and the touch screen 228 display text, alphanumeric information, data and graphic information via a series of menu choices to be selected by the user relating to the IMD 10, such as for example, status information, operating parameters, therapy parameters, patient status, access settings, software programming version, and the like. The display 226 may present screen shots (as shown in FIGS. 11-14) of a process (described in FIG. 5) to automatically determine ischemia detection parameters. The touch screen 228 accepts a user's touch input 227 when selections are made. The keyboard 230 (e.g., a typewriter keyboard 231) allows the user to enter data as well as interface with the telemetry subsystem 212.

Furthermore, custom keys 232 turn on/off 233 the external device 200, a printer 216 prints hard-copies of any reports 217 for a physician/healthcare worker to review or to be placed in a patient file, and speaker 214 provides an audible warning (e.g., sounds and tones 215) to the user in the event any abnormal situations occur while the external device 200 is being used. In addition, the external device 200 includes a parallel I/O circuit 222 to interface with a parallel port 223, a serial I/O circuit 224 to interface with a serial port 225, a floppy drive 220 to accept floppy diskettes 221, and a CD-ROM drive 218 that accepts CD ROMs 219.

The telemetry subsystem 212 may be used to communicate with IMD 10. The telemetry subsystem 212 includes a central processing unit (CPU) 234 in electrical communication with a telemetry circuit 238, which communicates with both an ECG circuit 236 and an analog out circuit 240. The ECG circuit 236 is connected to ECG leads 242, the telemetry circuit 238 is connected to a telemetry wand 244, and the analog out circuit 212 includes communication circuits, such as a transmitting antenna, modulation and demodulation stages (not shown), as well as transmitting and receiving stages (not shown) to communicate with analog outputs 246. The external device 200 may wirelessly communicate with the IMD 10 and utilize protocols, such as Bluetooth, GSM, infrared wireless LANs, HIPERLAN, 3G, satellite, as well as circuit and packet data protocols, and the like. The wireless RF link utilizes a carrier signal that is selected to be safe for physiologic transmission through a human being and is below the frequencies associated with wireless radio frequency transmission. Alternatively, a hard-wired connection may be used to connect the external device 200 to IMD 10 (e.g., an electrical cable having a USB connection).

Figure 4:
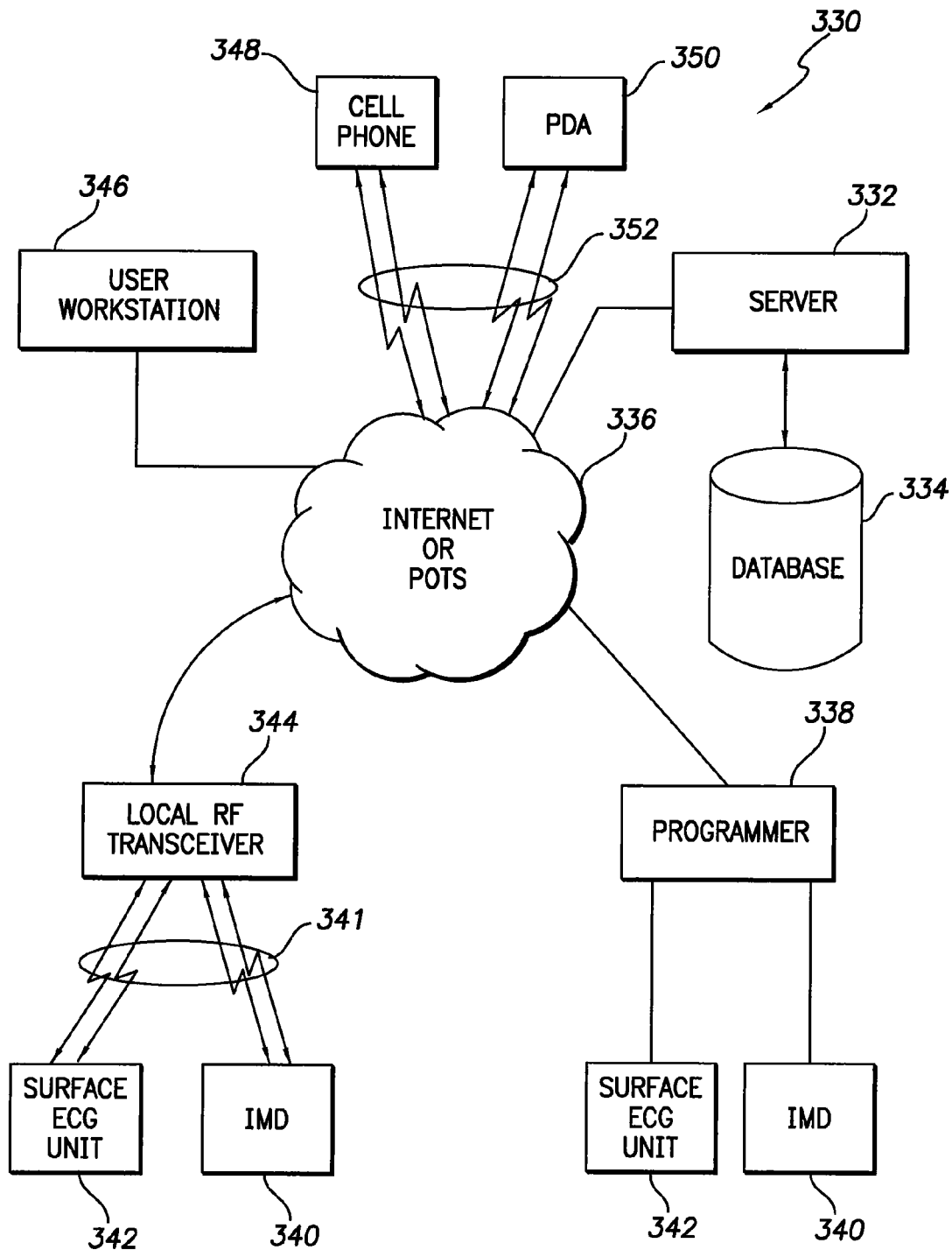
FIG. 4 illustrates a functional block diagram of a distributed processing system in accordance with an embodiment of the present invention.

FIG. 4 illustrates a distributed processing system 330 in accordance with an embodiment of this invention. The distributed processing system 330 includes a server 332 that is connected to a database 334, a programmer 338 (e.g. similar to external device 200 described above), a local RF transceiver 334 and a user workstation 346 electrically connected to a communication system 336 such as the internet, a voice over IP ("VoIP") gateway, or a local plain old telephone service ("POTS") such as a public switched telephone network ("PSTN"). Alternatively, the communication system 336 may be a local area network ("LAN"), a campus area network ("CAN"), a metropolitan area network ("MAN"), or a wide area network ("WAM"). The communication system 336 serves to provide a network that facilitates the transfer/receipt of cardiac signals, processed cardiac signals, histograms, trend analysis and patient status, and the like.

The server 332 is a computer system that provides services to other computing systems (e.g., clients) over a computer network. The server 332 acts to control the transmission and reception of information (e.g., cardiac signals, processed cardiac signals, ST segments, fiducial points, predefined offsets, ST segment traces, ischemia detection parameters, physiological state indicators, histograms, statistical analysis, trend lines, and the like). The server 332 interfaces with a communication system 336, such as the internet or a local POTS based telephone system, to transfer information between the programmer 338, the local RF transceiver 344, the user workstation as well as a cell phone 348, and a personal data assistant ("PDA") 350 to the database 334 for storage/retrieval of records of information. For instance, the server 332 may download to a cell phone 348 or PDA 350 the results of processed cardiac signals, as well as a baseline of a composite trace, a R-wave marker, a V-wave marker, a fiducial point, a ST window start point, a ST window end point, a ST window, a ST segment trace, a predefined offset, an ischemia detection parameter, physiologic state indicators, and the like. Additional information may be provided, for example, ST segment trends, or a patient's physiological state (e.g., is the patient having or has had an ischemia) based on previously recorded cardiac information. ST segment trends may include variations of ST segments occurring over a period of time. On the other hand, the server 332 may upload raw cardiac signals (e.g., unprocessed cardiac data) from surface ECG unit 342 or IMD 340 via the local RF transceiver 344 or the programmer 338.

Database 334 is any commercially available database that stores information in a record format in electronic memory. The database 334 stores information such as raw cardiac data, processed cardiac signals, statistical calculations (e.g., averages, modes, standard deviations), histograms, coronary burden information, cardiac trends (e.g., ST segment trends), fiducial points, predefined offsets, ischemia detection parameters, physiologic state indicators, and the like. The information is downloaded into the database 334 via the server 332 or, alternatively, the information is uploaded to the server from the database 334.

The programmer 338 is similar to the external device 200 described above and may reside in a patient's home, a hospital, or a physician's office. Programmer 338 interfaces with a surface ECG unit 342 and an IMD 340 (e.g., similar to ICD 10 described above). The programmer 338 may wirelessly communicate 341 with the IMD 340 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 338 to IMD 10 (e.g., an electrical cable having a USB connection). The programmer 338 is able to acquire cardiac signals from the surface of a person (e.g., ECGs), or the programmer is able to acquire intra-cardiac electrograms (e.g., IEGMs) from IMD 340. The programmer 338 interfaces with the communication system 336, either via the Internet or via POTS, to upload the cardiac data acquired from the surface ECG unit 342 or the IMD 340 to the server 332. The programmer 338 may upload more than just raw cardiac data. For instance, the programmer 338 may upload status information, operating parameters, therapy parameters, patient status, preference settings, software programming version, ST segment thresholds, predefined offsets, ischemia detection parameters, ST segment traces, R wave markers, V wave markers, baseline composite traces, fiducial points, a ST window start point, a ST window end point, and the like.

The local RF transceiver 334 interfaces with the communication system 336, either via the Internet or via POTS, to upload cardiac data acquired from the surface ECG unit 342 or the IMD 340 to the server 332. In one embodiment, the surface ECG unit 342 and the IMD 340 have a bi-directional connection with the local RF transceiver via a wireless connection 341. The local RF transceiver 344 is able to acquire cardiac signals from the surface of a person (e.g., ECG), or acquire an intra-cardiac electrogram (e.g., IEGM) from IMD 340. On the other hand, the local RF transceiver 344 may download stored cardiac data from database 334 or the analysis of cardiac signals from database 334 (e.g., ST segment variations, ST segment statistical analysis, ST segment trends, and the like) information to the surface ECG unit 342 or IMD 340.

The user workstation 346 may interface with the communication system 336 via the internet or POTS to download information via the server 332 from the database 334. Alternatively, the user workstation may download raw data from the surface ECG unit 342 or IMD 340 via either the programmer 338 or the local RF transceiver 344. Once the user workstation 346 has downloaded the cardiac information (e.g., raw cardiac signals, ST segments, and the like), the user workstation 346 may process the cardiac signals, create histograms, calculate statistical parameters, or determine cardiac trends and determine if the patient is suffering from ischemia or another physiological condition. Once the user workstation 346 has finished performing its calculations, the user workstation 346 may either download the results to the cell phone 348, the PDA 350, the local RF transceiver 344, the programmer 338, or to the server 332 to be stored on the database 334. Both programmer 338 and workstation 346 may present coronary burden information to a user. Furthermore, workstation 346 may have input leads (not shown) that collect cardiac signals in real-time. Alternatively, workstation 346 may acquire pre-recorded cardiac signals that were collected at an earlier time period from a memory, such as memory in programmer 338, memory in surface ECG unit 342, memory in IMD 340, or from database 334.

The programmer 338 may be utilized to collect a plurality of cardiac signals (e.g., intrinsic and paced) along with timing information, ST segment information, and heart rate information and then determine a composite baseline trace that is used to determine ischemia detection parameters based on at least one physiologic state indicator. The programmer 338 may be used to collect the cardiac signals from either the surface ECG unit 342 or the IMD 340, and then the programmer 338 may process the cardiac signals. By way of example, the programmer 338 may calculate the ischemia detection parameters in accordance with the process of FIGS. 5-10. Alternatively, the programmer 338 may transfer the raw cardiac information (e.g., cardiac signals, heart rates, time of each heart beat, ST segment value, ST segment traces, baseline values and the like) over the internet 336 to be stored in database 334. The raw cardiac information may be transferred over the Internet 336 to be processed by server 332 or user workstation 346. Optionally, IMD 340 may collect and process the raw cardiac information to determine i) a baseline composite trace, ii) physiologic state indicators and iii) the ischemia detection parameters. IMD 340 may then transfer the processed cardiac information as well as the ischemia detection parameters to either the programmer 338 or the local RF transceiver.

The IMD 340 may be used to collect and process the raw cardiac information as described above and then wirelessly communicate 341 the processed cardiac information to the local RF transceiver 344. Optionally, the local RF transceiver 344 may receive the raw cardiac information (e.g., cardiac signals, heart rates, time of each heart beat, ST segment traces, and the like) from the surface ECG unit 342 via a wireless link 341. The local RF transceiver 344 may then process the information to determine fiducial points, physiologic state indicators and ischemia detection parameters associated with a baseline composite trace. The local RF transceiver 344 may then transmit the processed cardiac information via the internet 336 to be stored by database 334. In addition, the local RF transceiver 344 may transmit the processed cardiac information via the internet 336 to be displayed on the cell phone 348, PDA 350, user workstation 346 or server 332. On the other hand, the local RF transceiver 344 may delay processing the information, and transfer the raw cardiac information via the internet to either be stored by the database 334 or to be processed by either the server 332 or the user workstation 346.

FIG. 5 illustrates a flow diagram for a process 400 to automatically determine ischemia detection parameters in accordance with an embodiment of the present invention. The process 400 maybe implemented by one or more devices and systems discussed above in connection with FIGS. 1-4. At 402, the process commences.

Figure 6A:
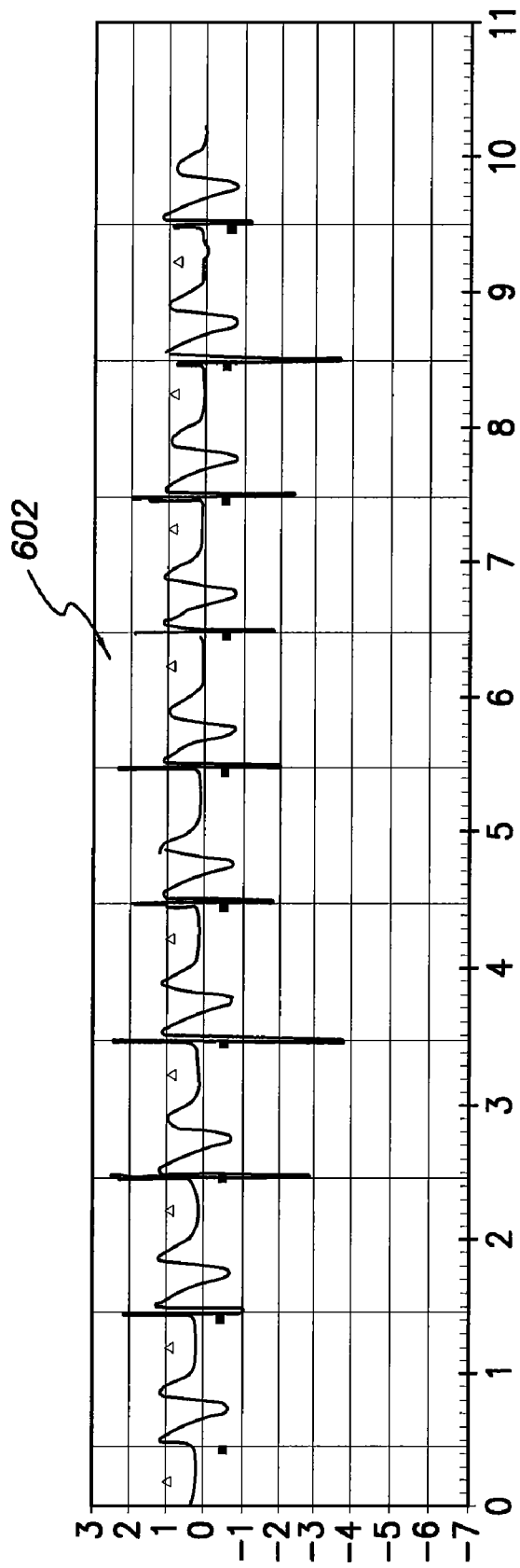
FIG. 6A illustrates a plurality of intrinsic cardiac data over a series of cardiac cycles utilized in accordance with an embodiment of the present invention.
Figure 7A:
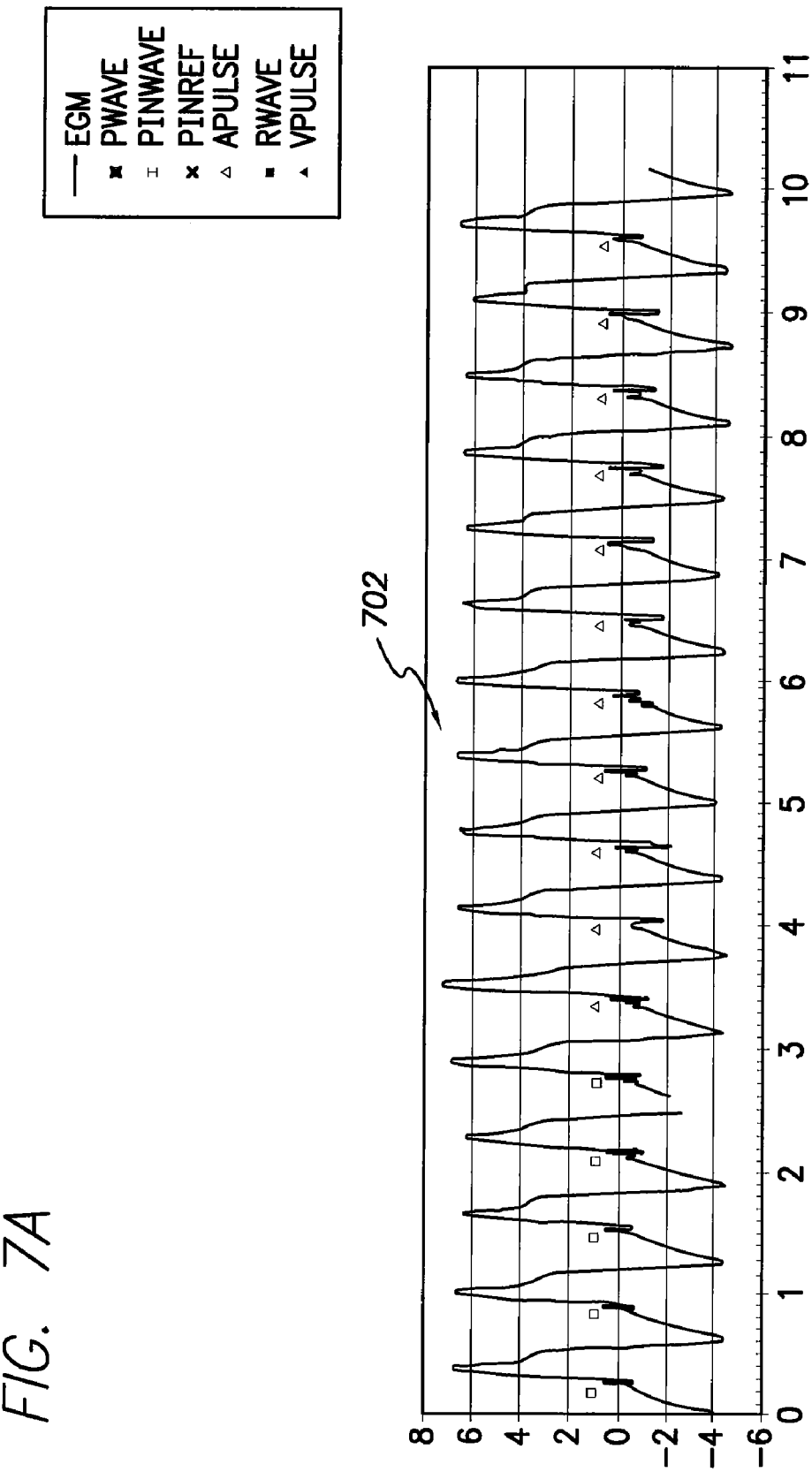
FIG. 7A illustrates a plurality of paced cardiac data over a series of cardiac cycles utilized in accordance with an embodiment of the present invention.

At 404, the process begins by collecting cardiac data over a series of cardiac cycles. The cardiac data may be a series of intrinsic heartbeats 602, as shown in FIG. 6A. Alternatively, the cardiac data may be a series of paced heartbeats 702, as shown in FIG. 7A, which are stimulated by either an atrial pulse generator or a ventricular pulse generator.

Figure 6B:
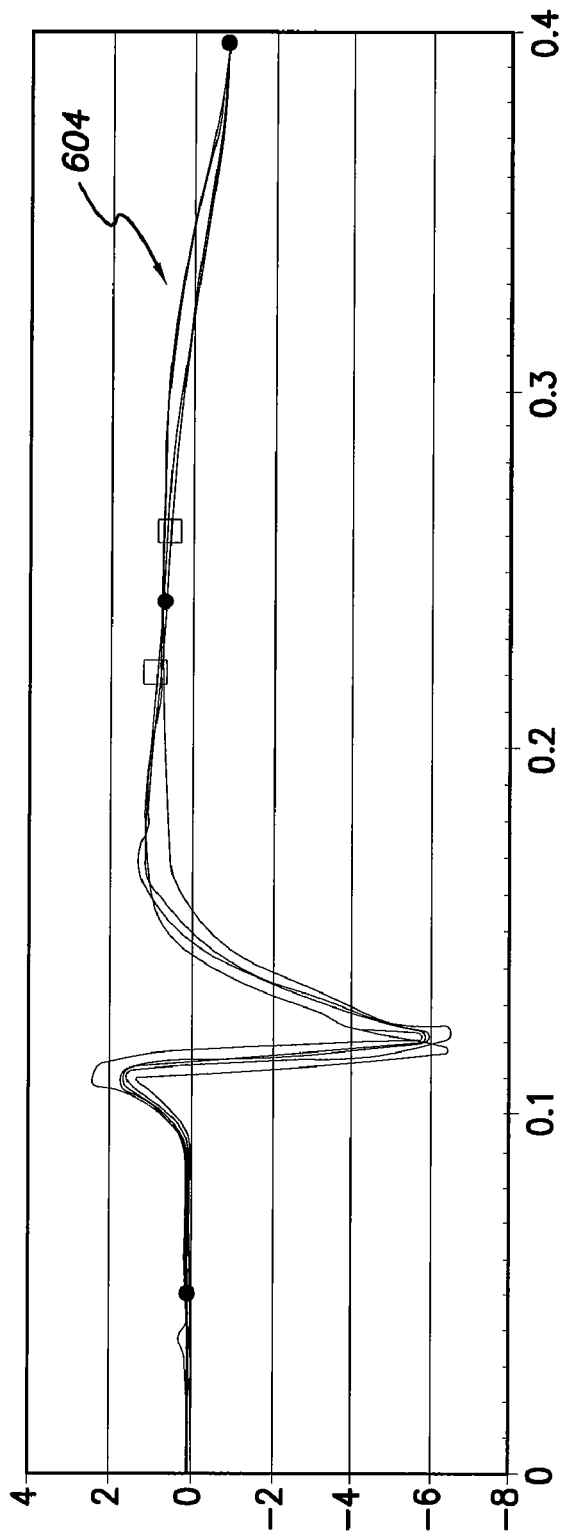
FIG. 6B illustrates creating a composite running average based on the intrinsic cardiac data shown in FIG. 6A formed in accordance with an embodiment of the present invention.
Figure 7B:
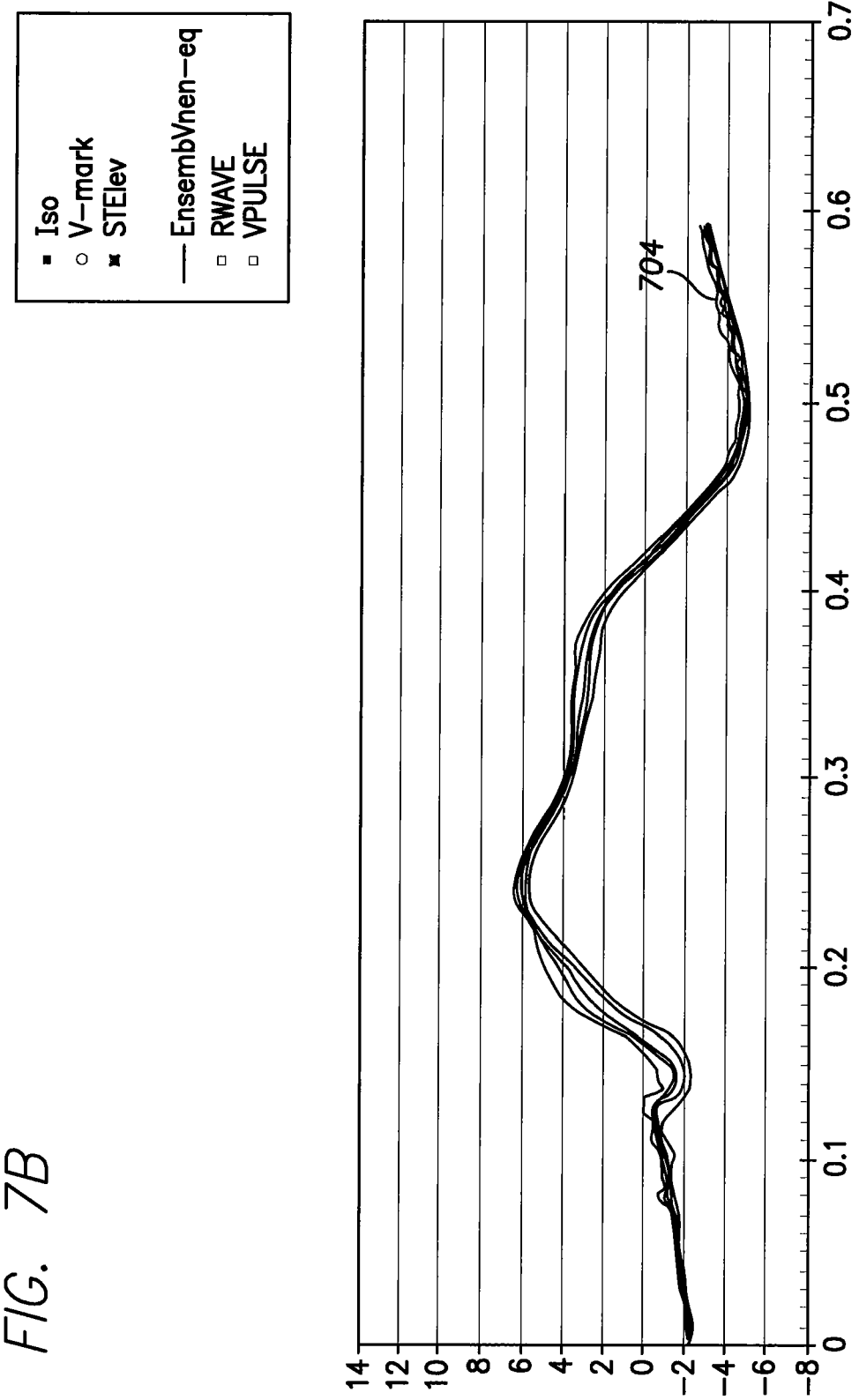
FIG. 7B illustrates creating a composite running average based on the paced cardiac data shown in FIG. 7A formed in accordance with an embodiment of the present invention.

At 406, the microcontroller 60 (shown in FIG. 2) or other data acquisition circuitry captures the cardiac data (e.g., intrinsic heartbeats or paced heartbeats) on a beat-by-beat basis for a predetermined period of time. The cardiac data 602 and 702 may be stored in memory 94 for later analysis or to be downloaded to an external device 102 through a telemetry circuit 100 (shown in FIG. 2). FIGS. 6B and 7B illustrate a running average 604 and 704 of the cardiac data composed from the heart beats 602 and 702 shown in FIGS. 6A and 7A respectively. Thus, FIG. 6B shows a running average of the ten intrinsic heart beats shown in FIG. 6A, and FIG. 7B shows a running average of the ten paced heart beats shown in FIG. 7A. The running averages 604 and 704 (e.g., an ensemble average) as shown in FIGS. 6B and 7B are composed by taking the average of a number of consecutive heart beats. The running averages 604 and 704 may be updated continuously with a new heart beat on a beat-by-beat basis or may be periodically updated. The updated running averages may be stored in memory 94 on a periodic basis. By averaging a plurality of cardiac data by a beat-by-beat basis over a predetermined period of time, the running average provides a clean, smooth signal without any noise, inconsistencies, artifacts, or aberrations that may exist in an individual heart beat. Thus, the running average for a set of intrinsic cardiac data may provide a baseline composite trace for an intrinsic running average, and the running average for a set of paced cardiac data may provide a separate baseline composite for a paced running average.

At 408, the process 400 automatically identifies at least one physiological state indicator in a PQRS complex. The physiological state indicators represent points in the cardiac cycle at which changes of interest occur (e.g., closing of the mitral valve) The physiologic state indicators are determined, by the ischemia parameter detection unit 111, based on changes in slope in the composite baseline trace after certain markers (e.g., P-wave, R-wave). To better understand the process at 408 to identify physiologic state indicators, reference is made to FIGS. 8 and 9 for intrinsic and paced cardiac events, respectively.

FIG. 8 illustrates a running average 800 (e.g., an ensemble average) of intrinsic cardiac data, hereafter called a composite intrinsic baseline 801. An R-wave marker 802 is determined as part of the QRS complex of the composite intrinsic baseline 801. Once the R-wave marker 802 is identified, the process, at 408, begins analyzing a shape of the composite intrinsic baseline 801 following the R-wave marker 802. The process at 408 identifies a series of changes in slope 804, 806, and 812. The changes in slope may be located by successively comparing adjacent points along the composite intrinsic baseline 801 with one another. Alternatively, slope changes may be recognized when the derivative of the composite intrinsic baseline 801 changes a sign from positive to negative or from negative to positive. Once the second and third changes in slope 806 and 812 are identified, they are used as the first and second physiologic state indicators. For example, the first slope change 804 corresponds to the point at which the mitral valve closes. The second slope change 806 corresponds to the minimum valley in the S-wave, which occurs at a point near the beginning of the isovolumic contraction phase. The third slope change 812 corresponds to a maximum valley in the T-wave which occurs during the reduced ejection phase of the heart cycle, before the isovolumic relaxation phase. Throughout, the slope changes 804, 806 and 812 are also referred to as physiologic state indicators 804, 806 and 812.

Returning to FIG. 5, at step 410, an ischemia detection window is determined based on the slope changes. For example, the slope changes 804, 806 and 812 are used to locate a first ischemia detection parameter (e.g., a start of the ST window) and a second ischemia detection parameter (e.g., an end of the ST window). The first ischemia detection parameter 808 (e.g., a ST window start point) is identified as a point along the composite intrinsic baseline 801 following the physiologic state indicator 806 by a positive offset 807 (e.g., about 25 msec). The second ischemia detection parameter 810 (e.g., a ST window end point) is identified as the point along the composite intrinsic baseline 801 preceding the physiologic state indicator 812 by a negative offset 809 (e.g., 35 msec). The positive and negative offsets 807 and 809 are programmable by the physician. FIG. 8 shows a ST window 814 that is determined based on a first ischemia detection parameter 808 and a second ischemia detection parameter 810 in the composite intrinsic baseline 801.

Optionally, a filter may be used to discriminate abnormalities in the composite intrinsic baseline 801, where the composite intrinsic baseline 801 changes slope again shortly after the second slope change 806 (e.g., when the slope of the composite intrinsic baseline 801 turns negative before the T-wave).

FIG. 9 illustrates an alternative example, in which the process at 408 and 410 is performed based on a paced event. FIG. 9 illustrates a running average 900 (i.e., an ensemble average) of paced cardiac data, hereinafter called a composite paced baseline 901. A V-wave marker 902 is determined as part of the QRS complex of the composite paced baseline 901. Once the V-wave marker 902 is identified, the process (at 408) identifies changes in slope 904, 906 and 912. The changes of slope 904, 906 and 912 may be located by successively comparing adjacent points along the composite paced baseline 901, or derivatives of the baseline 901, as discussed above. Next, at 408, the first ischemia detection parameter 908 (e.g., a ST window start point) is located at a point following the second physiologic state indicator 906 by a positive offset 907 (e.g., about 25 msec). The second ischemia detection parameter 910 (e.g., a ST window end point) is located at a point preceding the third physiologic state indicator 912 by a negative offset 909 (e.g., 1 msec to 200 msec). Thus, for example start the of the ST window 908 may be set 25 msec after the change in slope 906. The end of the ST window 910 may be set at 50 msec before the change in slope 912. Optionally, the offsets 907 and 909 maybe programmed to different values than the offsets 807 and 809. FIG. 9 shows a ST window 914 for the composite paced baseline 901 including the first ischemia detection parameter 908 and the second ischemia detection parameter 910.

Further, some patients having a paced rhythm may not show a plateau, such as the peak of the T-wave. Therefore, for such patients, the process 400 may determine a point where the derivative of the continuous paced baseline 901 is zero. Optionally, a filter may be used to discriminate abnormalities in the composite paced baseline 901, where the composite paced baseline 901 changes slope again shortly after the second slope change 906 (e.g., when the slope of the composite paced baseline 901 turns negative before the T-wave). Therefore, for both an intrinsic cardiac signal and a paced cardiac signal, the ST window maybe determined. Thus, while an IEGM signal may change shape depending on each patient's individual physiological condition, the underlying characteristics, such as the slope changes for intrinsic heart beats and paced heart beats, may remain the same and may be utilized to determine a first ischemia detection parameter and a second ischemia detection parameter.

Figure 10A:
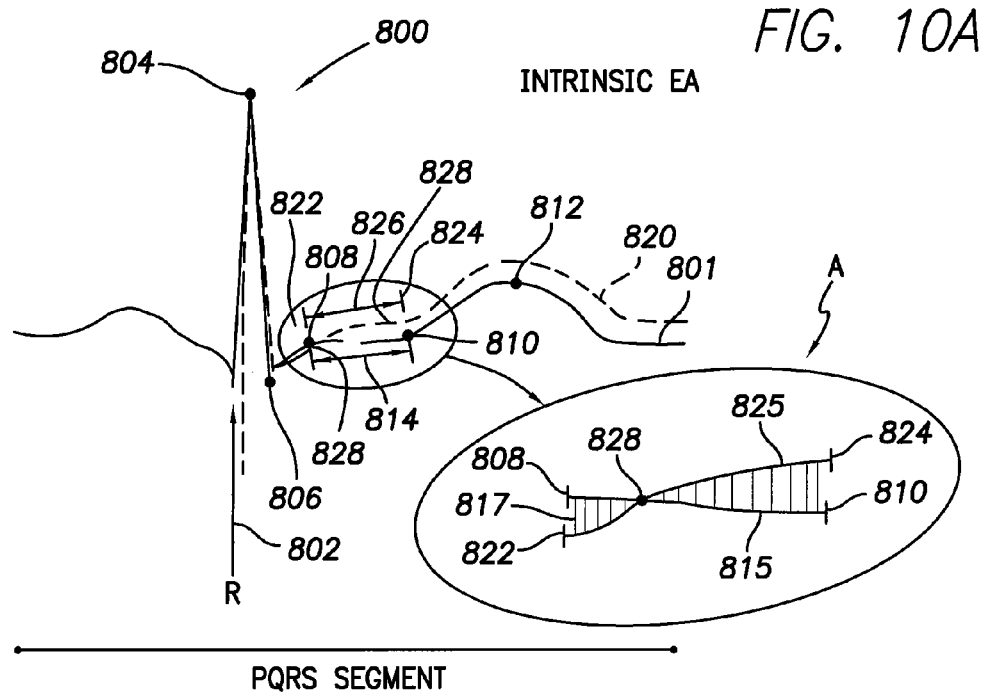
FIG. 10A illustrates a composite intrinsic baseline signal and an intrinsic heart beat signal normalized with one another based on a potential fiducial point in accordance with an embodiment of the present invention.
Figure 10B:
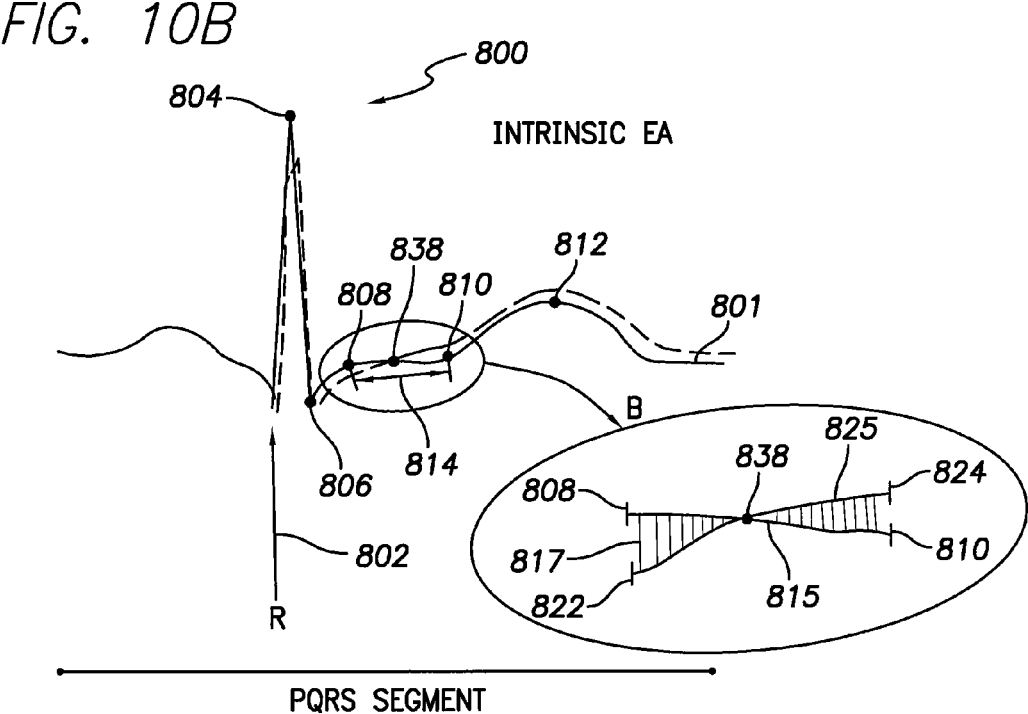
FIG. 10B illustrates a composite paced baseline signal and a paced and an intrinsic heart beat signal normalized with one another based on another potential fiducial point in accordance with an embodiment of the present invention.

Returning to FIG. 5, at 412 and 414, next a fiducial point within the ST window is identified. At 412, the process 400 continues by analyzing multiple potential fiducial points in the ST segment in the ST window 814 or 914 (FIGS. 8 and 9). A fiducial point represents a reference point in the ST window which is used to normalize each new cardiac signal (e.g., either a new intrinsic heart beat or a new paced heart beat) with the baseline trace (e.g., either a composite intrinsic baseline 801 or a composite paced baseline 901) before determining the amount of ST shift or variation in the cardiac signal relative to the baseline trace. The operation at 412 is described below in more detail in connection with FIGS. 10A and 10B. FIGS. 10A and 10B illustrate the composite intrinsic baseline 801 and a separate individual new cardiac trace or waveform 820 that has been collected during one cardiac cycle. The new cardiac waveform 820 may be acquired before, during or after the collection of cardiac data at 404.

The new cardiac waveform 820 should be overlaid, normalized or aligned onto the composite intrinsic baseline 801 before ST segment shifts within the waveform 820 can be determined relative to the composite intrinsic baseline 801. A ST window 826 for the intrinsic heart beat signal 820 is set by aligning the R-wave marker in the new cardiac waveform 820 and the R-wave marker in the composite intrinsic baseline 801. Then the start and end points of the ST window 808 and 810 from the composite intrinsic baseline 801 are used to define the start and end points of the ST window 822 and 824 from the new cardiac waveform 820. In general, a series of potential fiducial points may be analyzed, and a correlation/divergence is measured, for each fiducial point, between the new cardiac waveform 820 and the composite intrinsic baseline 801. FIG. 10A illustrates the correlation/divergence associated with one potential fiducial point 828. The new cardiac waveform 820 is normalized or overlaid on the composite intrinsic baseline 801 (as better shown in detail area A) such that they intersect at the potential fiducial point 828 within the ST windows 814 and 826. Next, the process 400 at 412 steps through a series of successive points along the baseline trace 815 within the ST window 814 and determines a difference (denoted by lines 817) at each point between the baseline trace 815 and the new segment trace 825 in the ST window 826 of the new cardiac waveform 820. The differences 817 are summed, for each point, along the ST window 814 to obtain a measure of correlation or divergence between the new segment trace 825 and baseline trace 815 when normalized to intersect at the fiducial point 828.

Next, a potential fiducial point 838 is selected (as shown in FIG. 10B) along the baseline trace 815. The baseline trace 815 and new segment trace 825 are normalized to intersect at the potential fiducial point 838 (as better shown in detail area B). A series of success points are processed to determine differences 817 between the baseline trace 815 and the new segment trace 825 at each point. The differences are summed to obtain a measure of correlation or divergence between the new segment trace 825 and baseline trace 815 when normalized to intersect at the fiducial point 838. The forgoing process is repeated until each potential fiducial point in the each ST window 814 is analyzed.

When detail A and B of FIGS. 10A and 10B are compared it can be seen that the area or difference between the baseline trace 815 and new segment trace 825 is greater when fiducial point 838 is used as compared to fiducial point 828. Thus, fiducial point 838 provides a larger difference than fiducial point 828. At 412, multiple fiducial points (e.g., 100) are analyzed to obtain an equal multiple of differences (e.g., 100). Once all potential fiducial points are analyzed, flow moves to 414.

At 414, one of the fiducial points is selected as a ST segment (STS) measurement. The fiducial point may be selected by determining the point in a ST segment that yields the maximum difference between a baseline trace 815 and a new segment trace 825. The fiducial point may be selected to show a physician or healthcare worker the greatest/largest difference between the current cardiac signal and the composite baseline signal running in the background.

A similar process may be performed to determine a fiducial point for paced waveforms. For instance, to determine the fiducial point between the composite paced baseline and the paced signal the process 400 compares corresponding points in the ST windows one data point at a time.

At 416, the selected fiducial point and automatically detected parameters (e.g., ST start and ST end) are presented to a physician. The presentation may include displaying the ischemia detection parameters on a display (e.g., computer, video, touch screen), a hard copy 217 (e.g., paper), on a PDA 350, a cell phone 348, a workstation 346, a monitor, an external programming device 102, and the like. At 418, the process terminates and may be repeated.

Figure 11:
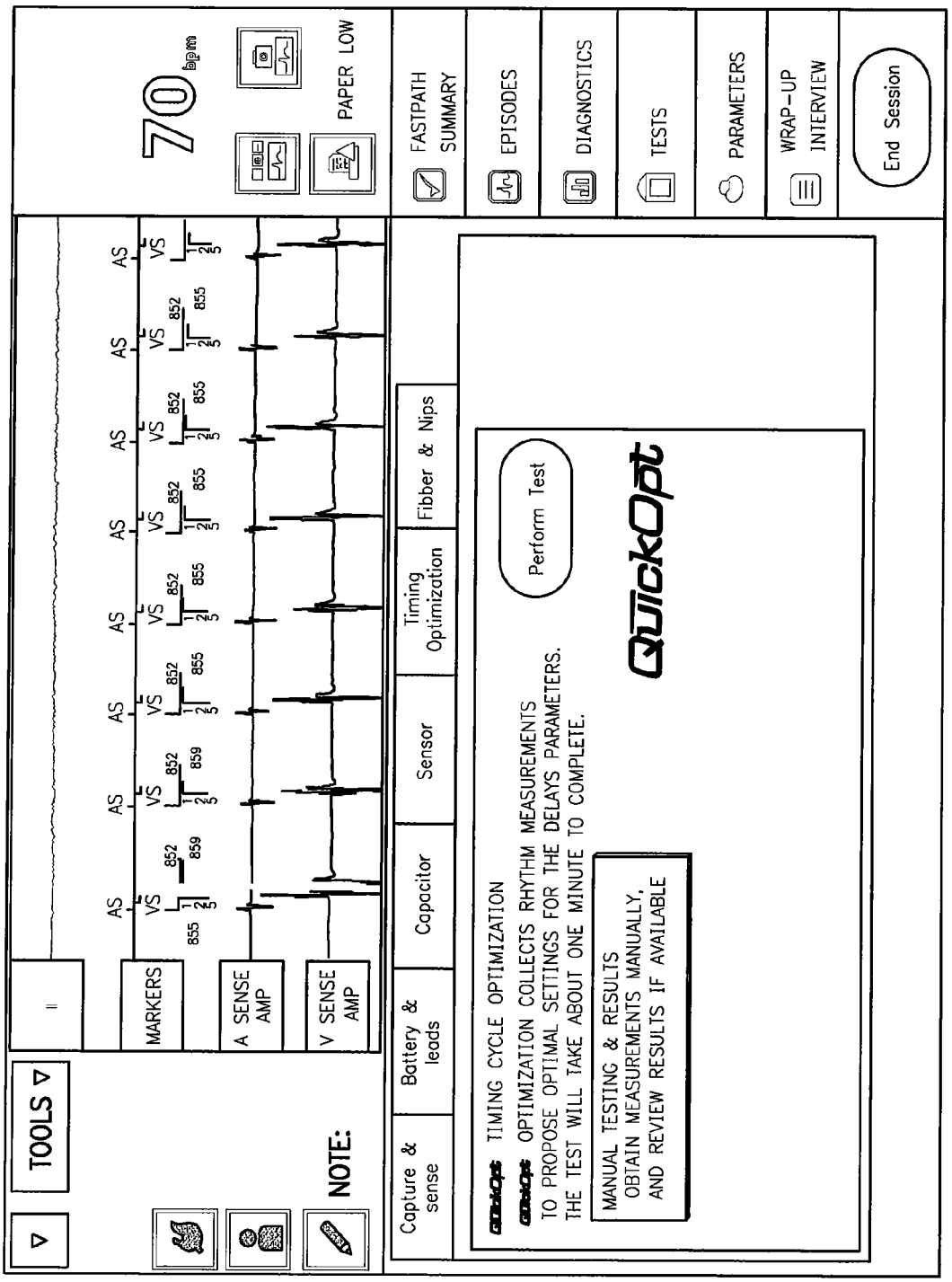
FIG. 11 illustrates a representative screen shot of an exemplary embodiment of the present invention.

FIGS. 11, 12, 13, and 14 depict representative screen shots of an exemplary embodiment of process 400 to automatically determine and program ischemia detection parameters. FIG. 11 illustrates a screen shot that displays two options for a user. One option is to run an automated test, and the other option is to run a manual test. If a manual test is selected, the user may have to obtain the results manually.

Figure 12:
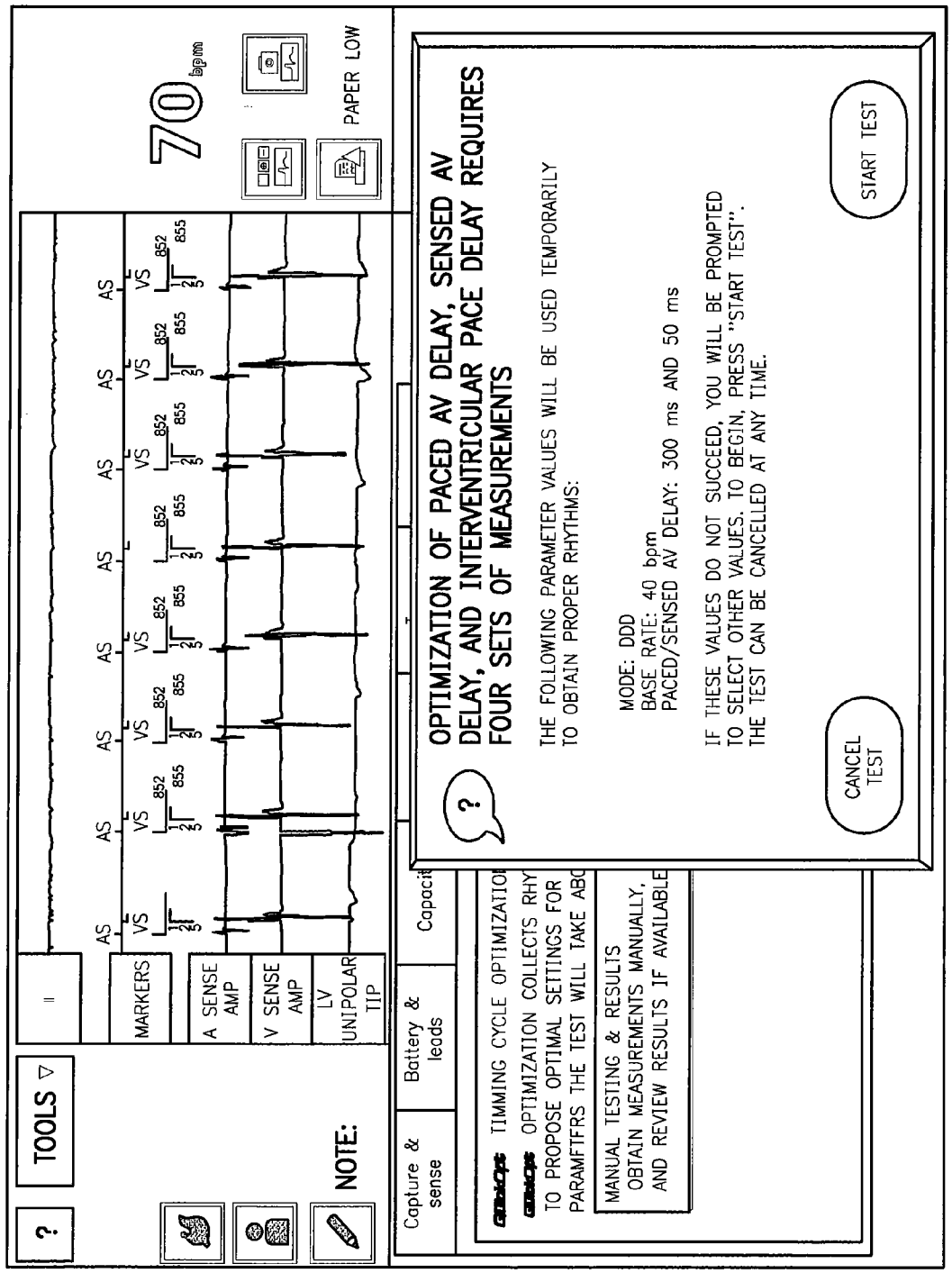
FIG. 12 illustrates a representative screen shot of an exemplary embodiment of the present invention.

FIG. 12 illustrates a screen shot that displays the ischemia detection parameters that have been temporarily programmed to provide test results. For instance, the exemplary screen shot shows that a user has selected to optimize a paced AV delay, a sensed AV delay, and an interventricular pace delay. As shown, a dual chamber pacing mode DDD, a base rate of 40 beats per minute (bpm), and a paced/sensed AV delay between 300 ms and 50 ms have been selected.

Figure 13:
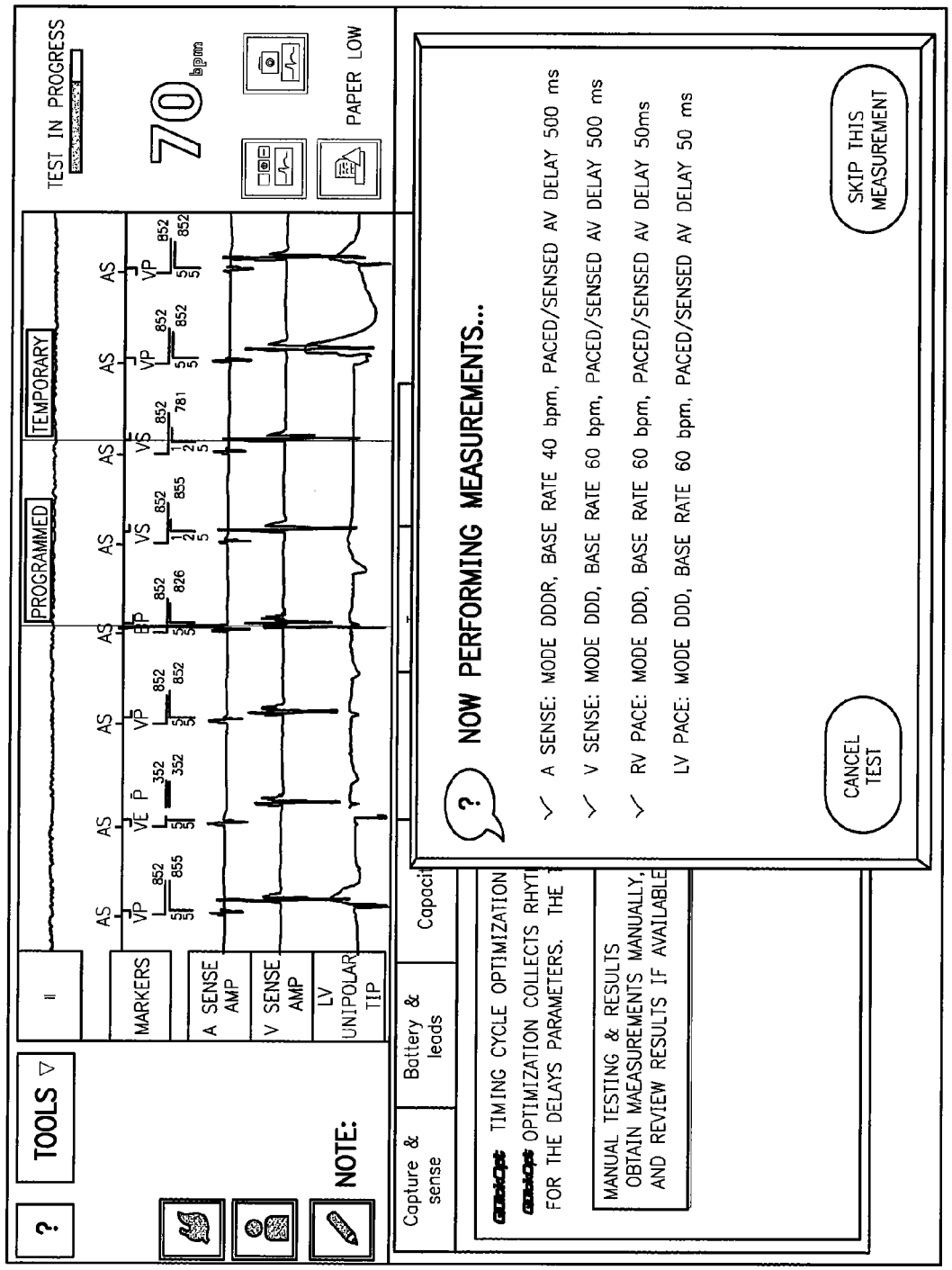
FIG. 13 illustrates a representative screen shot of an exemplary embodiment of the present invention.

FIG. 13 illustrates a test execution screen shot that provides a checklist of all the tests performed. For instance, the exemplary screen shot shows four measurements are in progress (e.g., A Sense, V Sense, RV Pace, and LV Pace), of which three measurements have been completed, as depicted by the "checkmark" (e.g., A Sense, V Sense and RV Pace) and one measurement is left to be completed (e.g., LV Pace).

Figure 14:
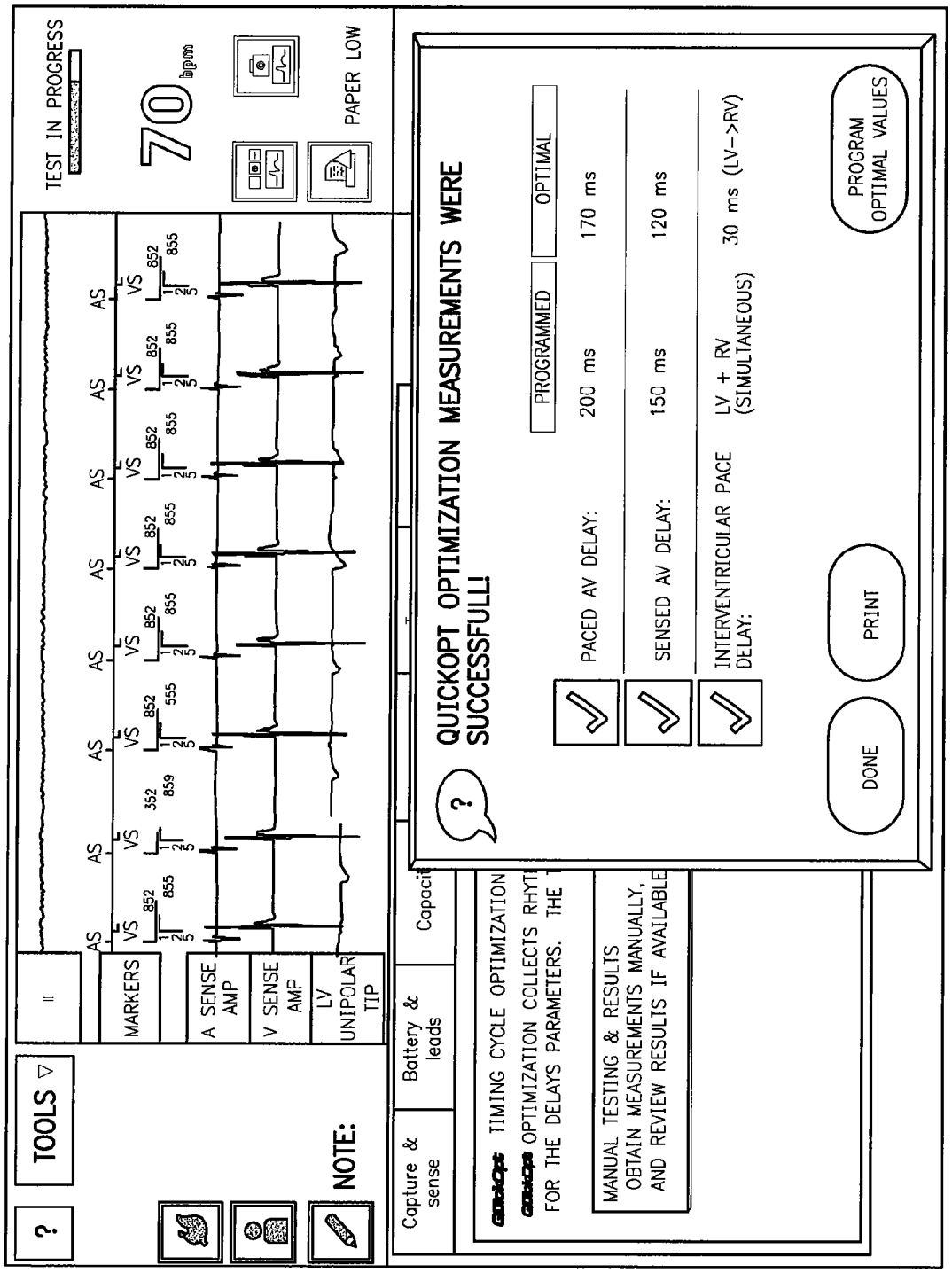
FIG. 14 illustrates a representative screen shot of an exemplary embodiment of the present invention.

FIG. 14 illustrates a screen shot that displays the test results for each user selected parameter, the currently programmed value for each parameter, and an optimal value for each parameter. For instance, the screen shot shows the following values for certain parameters, for example: a paced AV delay was programmed for 200 ms with an optimal value of 170 ms; a sensed AV delay was programmed for 150 ms with an optimal value of 120 ms; and an interventricular pace delay was programmed for LV+RV simultaneously with an optimal value of 30 ms (LV→RV).

In various embodiments of the invention, the method for automatically determining ischemia detection parameters can be implemented in software, hardware, or a combination thereof. The methods provided by various embodiments of the present invention, for example, can be implemented in software by using standard programming languages such as, for example, C, C++, Java, and the like.

In accordance with certain embodiments, methods and systems are provided that are able to ischemia detection parameters based on a baseline segment trace. The baseline segment trace includes an ischemia detection window that is used to automatically identify fiducial points. The fiducial points, ischemia detection parameters, and ischemia detection window along with baseline traces are presented to physicians in a manner that is insightful to potential monitored changes in ischemic events over a period of time.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for automatically determining ischemia detection parameters, comprising:
   obtaining a baseline trace indicative of a cardiac behavior;
   locating one of an R wave marker and a V wave marker in the baseline trace;
   analyzing the baseline trace to identify slope changes between points in the baseline trace;
   identifying a start point and end point in the baseline trace following the R wave or V wave marker as a function of the slope changes;
   determining an ischemia detection window based on the start and end points within the baseline trace, the baseline trace including a baseline segment within the ischemia detection window; and
   automatically determining a fiducial point by locating a fiducial point that yields a desired relation between the baseline segment and a new segment trace within the ischemia detection window, the ischemia detection window and fiducial point constituting ischemia detection parameters.

2. The method of claim 1, wherein determining an ischemia detection window based on the start and end points comprises determining a beginning of the ischemia detection window as a function of the start point plus an offset.

3. The method of claim 1, wherein determining an ischemia detection window based on the start and end points comprises determining an end of the ischemia detection window as a function of the end point minus an offset.

4. The method of claim 1, wherein identifying an end point in the baseline trace comprises identifying an end point in the baseline trace where the slope changes for the last time.

5. The method of claim 1, wherein identifying a start point in the baseline trace comprises identifying a point in the baseline trace where the slope changes for a second time following at least one of an R wave marker and a V wave marker.

6. The method of claim 1, wherein the determining an ischemia detection window based on the start and end points comprises determining an ischemia detection window based on the start and end points and at least one predefined offset.

7. The method of claim 1, wherein determining a fiducial point by locating a fiducial point that yields a desired relation between the baseline segment and a new segment trace within the ischemia detection window comprises determining the fiducial point by locating a fiducial point that gives a maximum difference between data values of the baseline segment and an actual segment trace during a ST window.

8. The method of claim 1, further comprising:
collecting cardiac data over a series of cardiac cycles
forming a baseline composite trace based on the cardiac data.

9. The method of claim 8, wherein the forming includes obtaining an ensemble average of the cardiac data over a series of cardiac cycles.

10. The method of claim 8, wherein the baseline composite trace represents a running average that is continuously updated.

11. A system for automatically determining ischemia detection parameters, comprising:
memory storing cardiac signals representative of cardiac activity of a patient over a period of time;
a processor configured to:
obtain a baseline composite trace indicative of a cardiac behavior;
locate one of an R wave marker and a V wave marker in the baseline trace;
analyze the baseline trace to identify slope changes between points in the baseline trace;
identify a start point and end point in the baseline trace following the R wave or V wave marker as a function of the slope changes;
determine an ischemia detection window based on the start and end points within the baseline composite trace, the baseline composite trace including a baseline segment within the ischemia detection window;
automatically identify a fiducial point by locating a fiducial point that gives a maximum difference between data values of the baseline segment and an actual segment trace; and
an output to present potential ischemia detection parameters.

12. The system of claim 11, wherein the processor determines a beginning point in the base line trace by identifying a point in the baseline trace where the slope changes for a second time following at least one of an R wave marker and a V wave marker.

13. The system of claim 11, wherein the processor determines an end point in the baseline trace by identifying a point in the baseline trace where the slope changes for the last time following at least one of an R wave marker and a V wave marker.

14. The system of claim 11, wherein the processor determines an ischemia detection window based on the start and end points and at least one predefined offset.

15. The system of claim 11, wherein the baseline composite trace is determined by obtaining an ensemble average of the cardiac data over a series of cardiac cycles, the ensemble average continuously being updated.

16. The system of claim 11, further comprising an implantable medical device (IMD) that includes the memory and processor, the memory in the IMD collecting baseline cardiac signals, the processor in the IMD determining an ensemble average.

* * * * *